US012685597B2

(12) United States Patent
Walter et al.

(10) Patent No.: US 12,685,597 B2
(45) Date of Patent: Jul. 21, 2026

(54) INTRAOPERATIVE STEREOTAXIC NAVIGATION SYSTEMS

(71) Applicant: VIVID SURGICAL PTY LTD, Crows Nest (AU)

(72) Inventors: William Lindsay Walter, Crows Nest (AU); Daniel Marsden-Jones, Crows Nest (AU)

(73) Assignee: VIVID SURGICAL PTY LTD (AU)

( * ) Notice: Subject to any disclaimer, the term of this patent is extended or adjusted under 35 U.S.C. 154(b) by 216 days.

(21) Appl. No.: 18/264,711

(22) PCT Filed: Feb. 8, 2022

(86) PCT No.: PCT/AU2022/050069
§ 371 (c)(1),
(2) Date: Aug. 8, 2023

(87) PCT Pub. No.: WO2022/165561
PCT Pub. Date: Aug. 11, 2022

(65) Prior Publication Data
US 2024/0299099 A1     Sep. 12, 2024

(30) Foreign Application Priority Data
Feb. 8, 2021     (AU) ................................ 2021900293

(51) Int. Cl.
*A61B 34/20*          (2016.01)
*A61F 2/46*           (2006.01)

(52) U.S. Cl.
CPC ............ *A61B 34/20* (2016.02); *A61F 2/4609*
(2013.01); *A61B 2034/2048* (2016.02);
(Continued)

(58) Field of Classification Search
CPC .... A61B 2034/2048; A61B 2034/2051; A61B 2090/397; A61B 34/20; A61B 17/1746;
(Continued)

(56) References Cited

U.S. PATENT DOCUMENTS

2010/0160771  A1 *   6/2010  Gielen ................... A61B 34/20
                                                        600/424
2013/0237811  A1      9/2013  Mihailescu et al.
(Continued)

FOREIGN PATENT DOCUMENTS

EP          1691860  B1      5/2011
EP          3486684  A1      5/2019
(Continued)

OTHER PUBLICATIONS

Extended European Search Report in European Application No. 22748745.1 mailed Nov. 20, 2024, 10 pages.
Notice of Reasons for Refusal in Japanese Application No. 193283 mailed Aug. 25, 2025, 6 pages.
International Search Report and Written opinion for Application No. PCT/AU2022/050069 mailed Mar. 21, 2022, 12 pages.

*Primary Examiner* — Samuel S Hanna

(57)          ABSTRACT

Intraoperative stereotaxic navigation system 10 for determining an orientation of a surgical tool (12) relative to a patient's anatomy located within a surgical environment (16). The system (10) includes a radar-based sensor (18) which is operable to define a field-of-view FOV 20 and determine at least one of relative distance to, direction to, and orientation of, one or more objects in the FOV 20, and a mount (24) configured to releasably secure the sensor (18) to one of the patient (26) and the tool (12) to allow the other of the patient (26) and the tool (12) to be within the FOV 20. A processor (28) is communicatively connectable with the radar-based sensor (18) and configured to determine the orientation of the tool (12) responsive to receiving at least one of relative distance, direction and/or orientation information, from the sensor (18), relating to at least one of the patient (26) and the tool (12), and receiving information
(Continued)

relating to orientation of the patient (26) relative to the surgical environment (16).

18 Claims, 3 Drawing Sheets

(52) U.S. Cl.
CPC ................. *A61B 2034/2051* (2016.02); *A61B 2034/2068* (2016.02); *A61F 2002/4681* (2013.01)

(58) Field of Classification Search
CPC .......... G01S 13/88; A61F 2/34; A61F 2/4609; A61F 2002/4681
See application file for complete search history.

(56) References Cited

U.S. PATENT DOCUMENTS

| | | | |
|---|---|---|---|
| 2015/0033246 A1 | 1/2015 | Gideon et al. | |
| 2015/0332465 A1 | 11/2015 | Schmidt et al. | |
| 2018/0007104 A1 | 1/2018 | Threlkeld et al. | |
| 2018/0071042 A1 | 3/2018 | Franjic et al. | |

FOREIGN PATENT DOCUMENTS

| | | | |
|---|---|---|---|
| JP | 2008526422 A | 7/2008 | |
| JP | 2020511239 A | 4/2020 | |
| JP | 2020123456 A | 8/2020 | |
| WO | 2018/085900 A1 | 5/2018 | |
| WO | 2019/036752 A1 | 2/2019 | |

* cited by examiner

INTRAOPERATIVE STEREOTAXIC NAVIGATION SYSTEMS

CROSS-REFERENCE TO RELATED APPLICATIONS

This application claims priority to Australian provisional patent application no. 2021900293, filed on 8 Feb. 2021, the content of which is incorporated herein in its entirety.

TECHNICAL FIELD

The present disclosure relates generally to intraoperative navigation systems typically used for guiding clinicians to implant a prosthesis into a patient during surgery.

BACKGROUND

In surgical procedures involving prosthetic implants, the orientation of a prosthesis relative to a patient's body at the time of being implanted can be critical to the success of the procedure.

For example, hip arthroplasty involves the replacement of the hip joint by a prosthetic implant. The implant can consist of different parts, including an acetabular cup designed to locate in the acetabulum (hip socket). The acetabular cup is located in position using an acetabular cup impactor, which generally takes the form of an elongate rod, having the cup releasably secured at one end, and which is used to insert and orient the cup in the acetabulum. To ensure that an acetabular cup functions correctly, and does not wear significantly or cause damage to a patient, it is important that the cup is oriented and positioned correctly in the acetabulum.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In one aspect of the present disclosure, there is provided an intraoperative stereotaxic navigation system for determining an orientation of a surgical tool relative to a patient's anatomy located within a surgical environment, the system including: a radar-based sensor operable to define a field-of-view (FOV) and determine at least one of relative distance to, direction to, and orientation of one or more objects in the FOV; a mount configured to releasably secure the radar-based sensor to one of the patient and the tool to allow the other of the patient and the tool to be within the FOV; and a processor communicatively connectable with the radar-based sensor and configured to determine the orientation of the tool responsive to receiving at least one of relative distance, direction, and orientation information, from the radar-based sensor, relating to at least one of the patient and the tool, and receiving information relating to the orientation of the patient relative to the surgical environment.

The processor may be configured to determine the orientation of the tool responsive to receiving at least one of relative distance information and direction information, from the radar-based sensor, relating to one or more points defined by a portion of the patient's anatomy or the tool. At least two points may be defined by one of the patient's anatomy and the tool, and, responsive to receiving at least one of relative distance information and direction information, from the radar-based sensor, relating to the at least two points, the processor is configured to determine a vector defined between the at least two points to determine a position of the patient's anatomy or the tool.

The system may further include at least one tracker defining at least one point and configured to be mounted to one of the patient, the tool and the surgical environment, and the processor may be configured to determine the orientation of the tool responsive to receiving at least one of relative distance information and direction information, from the radar-based sensor, relating to the, or each, tracker. At least two points may be defined by the at least one tracker, and, responsive to receiving at least one of relative distance information and direction information, from the radar-based sensor, relating to the at least two points, the processor is configured to determine a vector defined between the at least two points to determine a position of the patient's anatomy, the tool, or the surgical environment. The mount may be configured to releasably secure the radar-based sensor to the patient, and the, or each, tracker may be configured to be mounted to the tool. The mount may be configured to releasably secure the radar-based sensor to the surgical tool, and the, or each, tracker may be configured to be mounted to the patient. Responsive to receiving the at least one of relative distance information and direction information relating to the, or each, tracker, the processor may be configured to determine at least one of: an orientation of the surgical tool, a velocity of the surgical tool, an acceleration of the surgical tool, an angular displacement of the surgical tool, an angular velocity of the surgical tool, and an angular acceleration of the surgical tool.

They system may further comprise a plurality of the trackers, and at least some of the trackers may be configured to be mounted to the surgical environment, and responsive to receiving the at least one of relative distance information and direction information relating to the at least some of the trackers, the processor may be configured to determine the orientation of the patient relative to the surgical environment. The, or each, tracker may be a reflective marker.

The system may further include an orientation sensor communicatively connectable to the processor and operable to determine the orientation of the patient relative to the surgical environment. The orientation sensor may be operable to determine at least two vectors defined by the patient. The orientation sensor may be releasably securable to one of the radar-based sensor and the mount. The orientation sensor and the radar-based sensor may be mounted to a common housing.

The mount may be configured to releasably secure the radar-based sensor to the patient, and the system may include a further mount configured to releasably secure a further radar-based sensor to the tool, and a plurality of the trackers, at least one tracker may be configured to be mounted to one of the further mount and the further radar-based sensor to be within the FOV of the radar-based sensor, and at least one other tracker may be configured to be mounted to the patient to be within the FOV of the further radar-based sensor, and the processor may be communicatively connected to the further radar-based sensor to receive the relative distance information.

The system may further include at least one further radar-based sensor configured to emit signals and be mounted to one of the patient, the tool, and the surgical environment to allow being within the FOV, and wherein the radar-based sensor is operable to receive the signals from the further radar-based sensor, and wherein the processor is configured to determine the orientation of the tool respon-sive to receiving at least one of relative distance information and direction information, from the radar-based sensor, relating to the further radar-based sensor.

In another aspect of the present disclosure, there is provided an intraoperative stereotaxic navigation system for determining an orientation of a surgical tool relative to a patient's anatomy located within a surgical environment, the system including: a radar-based sensor operable to define a field-of-view (FOV) and determine at least one of relative distance to, direction to, and orientation of one or more objects in the FOV; a mount configured to releasably secure the radar-based sensor relative to the environment; a plural-ity of trackers, each configured to be mounted to one of the patient and the tool to allow each tracker to be within the FOV; and a processor communicatively connected with the radar-based sensor and configured to determine the orienta-tion of the tool responsive to receiving at least one of relative distance, direction, and orientation information relating to each of the trackers.

In yet another aspect of the present disclosure, there is provided an intraoperative stereotaxic navigation system, including: a surgical tool including a radar-based sensor operable to define a field-of-view (FOV) and determine at least one of relative distance to, direction to, and orientation of one or more objects in the FOV; and a processor com-municatively connectable with the radar-based sensor and configured to determine an orientation of the tool relative to a patient's anatomy responsive to receiving at least one of relative distance, direction, and orientation information, from the radar-based sensor, relating to at least one of the patient's anatomy and the tool, and receiving information relating to the orientation of the patient relative to a surgical environment surrounding the patient.

In any of the aspects of the present disclosure, the mount may be an integral portion of the, or each, radar-based sensor, the surgical tool may be an acetabular cup impactor, the, or each, radar-based sensor may be a millimetre wave sensor, and the patient's anatomy may comprise a bone.

Any of the aspects of the present disclosure may comprise a plurality of the radar-based sensors and a respective plurality of mounts. In such embodiments, responsive to receiving at least one of relative distance, direction and orientation information from the plurality of radar-based sensors, the processor may be configured to determine a relative position of two or more of the radar-based sensors. In such embodiments, the processor may be further config-ured to determine the orientation of the tool responsive to determining the relative position of the two or more radar-based sensors.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the disclosure will now be described by way of example only with reference to the accompanying drawings in which.

DETAILED DESCRIPTION OF EXEMPLARY EMBODIMENTS

Figure 1:
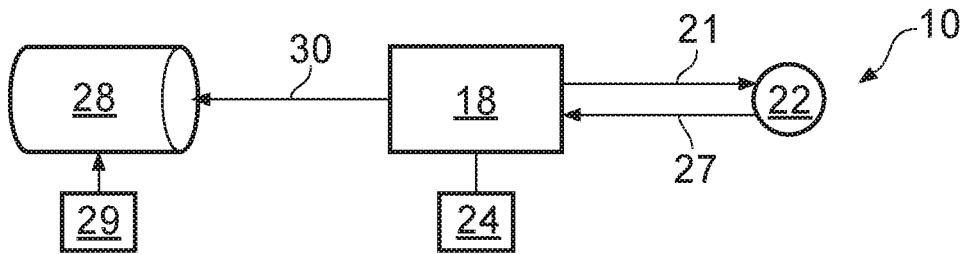
FIG. 1 shows a schematic of an embodiment of an intraoperative stereotaxic navigation system.

In the drawings, reference numeral 10 generally desig-nates an intraoperative stereotaxic navigation system 10 for determining an orientation of a surgical tool 12, such as an acetabular cup impactor, relative to a patient's anatomy located within a surgical environment 16. The system 10 includes a radar-based sensor 18 which is operable to define a field-of-view (FOV) 20 (FIG. 2) and determine at least one of relative distance to, direction to, and orientation of, one or more objects in the FOV 20, and a mount 24 configured to releasably secure the sensor 18 to one of the patient 26 and the tool 12 to allow the other of the patient 26 and the tool 12 to be within the FOV 20. The system 10 further includes a processor 28 communicatively connectable with the radar-based sensor 18 and configured to determine the orientation of the tool 12 responsive to receiving at least one of relative distance, direction and/or orientation information, from the sensor 18, relating to at least one of the patient 26 and the tool 12, and receiving information relating to orientation of the patient 26 relative to the surgical environment 16.

FIG. 1 is a schematic diagram of the system 10. The radar-based sensor 18 is configured to transmit and receive electromagnetic (EM) signals 21, 27. In some embodiments, the sensor 18 is configured as a "millimetre (mm) wave" radar sensor such that the transmitted signals 21 have a wavelength in the millimetre range, and a frequency of around 24-300 GHz, and most typically above 74 GHz. In some embodiments, the radar-based sensor 18 is operable to transmit a "chirp" of signals 21 comprising a range of frequencies. In other embodiments (not illustrated), the sensor 18 is configured as an alternative radar-type sensor, such as a high frequency radio wave sensor.

The sensor 18 includes at least one antenna (not illus-trated) operable to transmit signals 21 and receive signals 27, such as signals 27 being reflected back to the sensor 18 from the object 22 as illustrated in FIG. 1. In some embodi-ments, a second sensor 18 may be arranged in the FOV of a first sensor 18 such that the first sensor 18 may receive the signals 21 transmitted from the second sensor 18.

In some embodiments, the sensor 18 includes a plurality of antennas arranged to be spaced apart from each other. This arrangement of multiple antennas allows defining the FOV, such as by beam forming. It will be appreciated that the FOV is the region over which the signals 21, 27 can be emitted or received by the one or more antennas. The number and arrangement of the antennas is configured to achieve a required angular resolution, where a greater num-ber of antennas may be employed to enhance system per-formance, particularly with respect to angular resolution and accuracy of measurement. For example, the antennas may be configured as a cascaded radar arrangement.

In some embodiments, the processor 28 is hosted remotely from the sensor 18 in a computing device, such as a smartphone or a server, and the processor 28 and the sensor 18 are communicatively connected, by wireless or wired connection, in some embodiments being via the Internet. In other embodiments, the processor 28 is configured to be an integral component of the sensor 18. The surgical tool 12 may be any suitable tool where determining orientation, position, velocity, or the like, relative to the patient 26, would be beneficial, such as an acetabular cup impactor, a reamer, or a cutting block.

The sensor 18 is operable to transmit the electromagnetic signals 21 and receive signals 27 reflected from one or more points defined by an object 22 within the FOV 20. The signals 21 are transmitted as pulses and/or as frequency modulated continuous waves (FMCW). The received signal 27 is processed by the sensor 18, and/or the processor 28, to determine relative spacing between the one or more localised points and the sensor 18 (also referred to as "range"). The sensor 18 and/or the processor 28 is configured to determine the relative distance to within 2.5 mm. For some applications, the sensor 18 is configured to determine relative distance within 0.25 mm, and for particular applications to within 0.1 mm, at a range of up to approximately 2.5 m.

It will be appreciated that relative distance may be determined in a number of conventional ways, such as calculating the time of flight of the pulsed signal 27, comparing phases of the transmitted electromagnetic signal 21 and the received signal 27, or a combination of these and other approaches.

The radar-based sensor 18 is operable to measure the relative distance of one or more points in the FOV, such as defined by the object 22 and/or defined by the location of signal transmission from another sensor 18. Operating the sensor 18 in this way allows the sensor 18 and/or the processor 28 to determine a vector relating to the one or more points, the vector comprising magnitude and direction, which consequently allows determining a position and/or orientation of the object 22. For example, where two points are identified in the FOV, the sensor 18 and/or processor 20 may be configured to determine a first vector between the sensor 18 and one of the points, to determine the position of the object 22, and a second vector between the two points, to determine the orientation of the object 22.

In some embodiments, the radar-based sensor 18 is operable to determine velocity of the object 22. It will be appreciated that calculating velocity of the object 22 may be achieved according to conventional approaches, for example, by analysing the Doppler Effect of the reflected pulsed signals 27, calculating a change in position over time, phase comparisons, time of flight, or applying a differentiation of position.

The information received by the processor 28 relating to orientation of the patient 26 relative to the environment 16 typically involves determining at least one vector defined by the patient 26, such as a longitudinal axis. The at least one vector may include a transverse vector extending across the patient's 26 body, e.g. across the chest or pelvis, and a longitudinal vector along the patient's 26 body, e.g. from head to foot, typically being perpendicular to the transverse vector. These vectors may be obtained by a range of approaches, such as direct measurement of the patient 26 and/or environment 16 with one or more sensors, manual input of data by a clinician, and/or by obtaining data from scans of the patient's 26 body with an external system, such as a fluoroscopy system.

For some applications, preoperative or intraoperative imaging is used to create a three-dimensional (3D) model of the patient's anatomy. Alternatively, a generic 3D model of patient anatomy is employed. The 3D model may be registered to the sensor 18 by a number of different methods including: probing the anatomy with a pointer that is tracked by the sensor 18, direct visualisation of the anatomy with the sensor 18, or using a patient specific 3D part shaped to specifically fit to the anatomy.

Direct measurement of the patient 26 may involve measuring between two points spaced symmetrically across the patient 26 to derive the transverse vector, and rotating the patient, by an articulated surgical table or platform (not shown), about an axis of rotation of the platform to derive the longitudinal vector. In some embodiments, the processor 28 is configured to perform a cross-product function between the transverse vector and the longitudinal vector to generate a height vector, which is perpendicular to a virtual plane defined by the transverse vector and the longitudinal vector. In other words, three orthogonal vectors are measured and/or generated to allow defining three orthogonal axes. This process allows determining a virtual three-dimensional (3D) reference system with the origin at the intersection of the three vectors. This may then be processed, in conjunction with the reflected signals 27 received by the sensor 18, to determine the location, and orientation, of the object 22 in space, for example, relative to the patient 26.

It will be appreciated that the virtual 3D reference system may be determined without an orientation sensor, for example, by using a predetermined 3D axis formed by measuring two vectors defined by the surgical environment 16 using any suitable means, such as a rod fitted with a tracker, and generating the third axis based on the cross-product of the two measured vectors. It will also be understood that the virtual 3D reference system may be determined by measuring points defined by the surgical environment 16 and/or the patient's anatomy using a pointer fitted with a tracker (not illustrated), In some embodiments, the system 10 includes an orientation sensor 29, typically in the form of an inertial measurement unit (IMU) or altitude heading reference system (AHRS). The orientation sensor 29 is communicatively connected to the processor 28, and, in some embodiments, also to the radar-based sensor 18, via a wired or wireless connection. The orientation sensor 29 is typically securable relative to the radar-based sensor 18, such as being configured for releasably engaging with one of the sensor 18 and the mount 24, or being fixed to the sensor 18 by a common housing. The orientation sensor 29 is operable to allow the orientation of the patient 26 relative to the surgical environment 16 to be determined by measuring a gravity vector, typically concurrently with rotating the patient 26, or part of the anatomy of the patient 26, about an axis. This is processed, by the processor 28, in combination with the transverse vector, to determine the longitudinal vector. It will be appreciated that the orientation sensor 29 may alternatively or additionally include any suitable sensor(s), such as a plurality of gyroscopes, accelerometers, and the like.

In addition to measuring distance to, direction to, and/or velocity of the object(s) 22, the radar-based sensor 18 may be configured to measure these values at two or more separate locations on the same object 22 to determine orientation, acceleration, angular displacement, angular velocity and angular acceleration of the object 22. Similarly, it will be appreciated that the sensor 18 may be configured to measure values of two or more objects 22 concurrently.

Operating the sensor 18 causes some of the transmitted signals 21 to be absorbed or scattered by the object 22. Absorbance and scattering of signals allows the processor 28 to differentiate between different features or regions of the object 22 responsive to the detected reflected signals 27 or absence of reflected signals. For example, where the object 22 is formed from different materials, defines different surface finishes, or has a variable internal structure, the reflected signals 27 may be scattered and therefore more diffuse, or may not reflect the transmitted signal(s) 21. In the surgical environment, this can be useful to allow the processor 28 to distinguish between apparatus and patient, and aspects of the patient's anatomy, such as tissue, blood, and bone.

Figure 2:
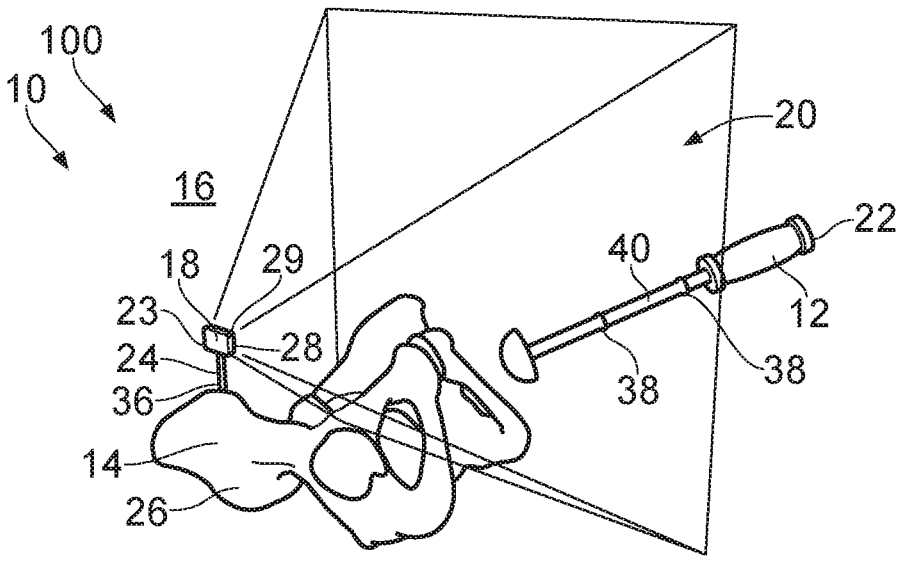
FIG. 2 shows a perspective view of another embodiment of the intraoperative stereotaxic navigation system shown in FIG. 1, in use.

FIG. 2 shows one embodiment 100 of the system 10 in which the radar-based sensor 18 is configured to be releasably secured to the patient's anatomy, which, in this embodiment, is the patient's bone 14, via the mount 24. In this embodiment, the mount 24 includes a bone pin 36 to allow releasably engaging the bone 14. The orientation sensor 29 and the processor 28 are secured relative to the radar-based sensor 18 in a common housing 23. It will be appreciated that two or more bone pins 36 may be used to releasably engage the radar-based sensor 18 to the bone 14.

The system 100 also includes a plurality of reflective (passive) trackers 38 mounted to the surgical tool 12 to be positioned within the FOV 20 of the sensor 18. The trackers 38 are configured to optimise reflection of the transmitted signals 21 to enhance determining, by the sensor 18, relative distance to, direction to, and/or orientation of the trackers 38.

The trackers 38 are configurable in a range of forms to enhance reflection of the signals 27, such as including baubles, rings, and/or collars securable to a shaft 40 of the tool 12. In some embodiments, the trackers 38 include corner reflectors defining three perpendicularly arranged planar surfaces to form an internal corner. Corner reflectors are configured to reflect a transmitted signal 21 in the incident direction, which can enhance detection of reflected signals 27 by the sensor 18.

Mounting the sensor 18 and trackers 38 as shown in FIG. 2 means that the sensor 18 has a substantially stationary frame of reference, while the trackers 38 move when a clinician adjusts a position of the tool 12. The trackers 38 therefore define reference points which move, which allows the processor 28 to determine, and monitor, the orientation of the tool 12, responsive to receiving at least one of relative distance, direction, and/or orientation information relating to the trackers 38 from the sensor 18. It will be appreciated that the processor 28 may also determine the velocity, position, acceleration, and/or any of the other previously mentioned parameters of the tool 12 with the sensor 18 and trackers 38 mounted as shown in FIG. 2.

Whilst the tool 12 is shown carrying a pair of trackers 38 it will be appreciated that this is an exemplary arrangement, and that more or less trackers 38 may be mounted to the tool 12 to allow determining position and/or orientation of the tool 12 from measurements obtained by the sensor 18. Furthermore, it will be appreciated that the passive trackers 38 may be substituted for active, signal-emitting trackers (not shown). Such active trackers are typically powered and operable to emit an EM signal to allow detection by the sensor 18.

In some embodiments (not illustrated), additional trackers 38 are mounted to the surgical environment 16. When these are arranged within the FOV 20 of the sensor 18, this allows the processor 28 to determine the orientation of the patient 26 relative to the surgical environment 16. This typically involves detecting movement of the patient 26 relative to the trackers 38 mounted to the environment 16, such as by the patient 26 being rotated about an axis defined by the surgical platform.

Figure 3:
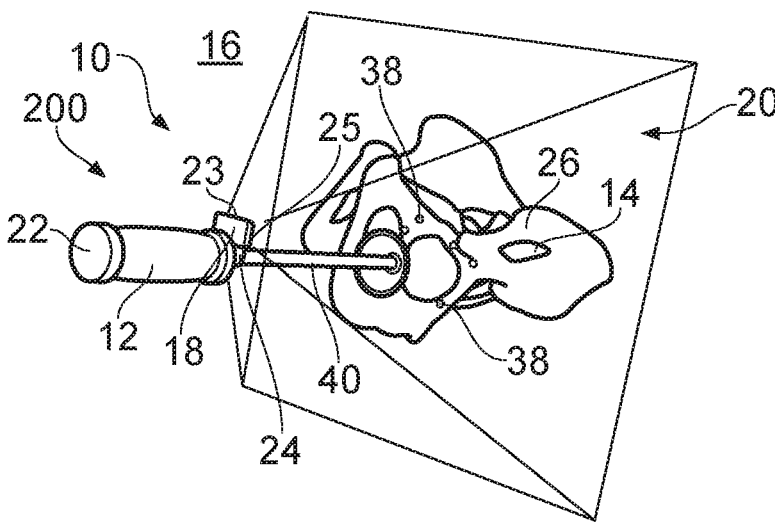
FIG. 3 shows a perspective view of another embodiment of the intraoperative stereotaxic navigation system shown in FIG. 1, in use.

FIG. 3 shows another embodiment 200 of the system 10 in which the radar-based sensor 18 is configured to be releasably secured to the shaft 40 of the tool 12 via the mount 24. In this embodiment, the mount 24 is an integral portion of the sensor 18 and includes a clamping mechanism 25 operable to releasably grip the tool 12. The orientation sensor 29 (not shown) is separate from the radar-based sensor 18 and configured for securing to the patient 26, for example, via a bone pin-type mount. The processor 28 is located remotely from, and communicatively connected to, the sensor 18.

The trackers 38 are configured to be mounted to the patient 26, in the illustrated embodiment, being mountable directly to the bone 14, to be arranged within the FOV 20 of the sensor 18. In this embodiment, the trackers 38 remain substantially stationary while the sensor 18 is movable responsive to the clinician moving the tool 12. This is effectively the inverse arrangement of the embodiment 100 shown in FIG. 2 and therefore allows orientation of the tool 22 to be determined by the processor 28 in substantially the same way.

In some embodiments (not illustrated), the embodiment 200 of FIG. 3 is alternatively configured such that the radar-based sensor 18, and optionally also the processor 28, are integrated with the tool 12, and the mount 24 is omitted. Such embodiments are however only suitable for applications where it is practical and cost-effective to clean and sterilise the tool 12 while maintaining functionality of the integrated electronics.

Figures 4, 5:
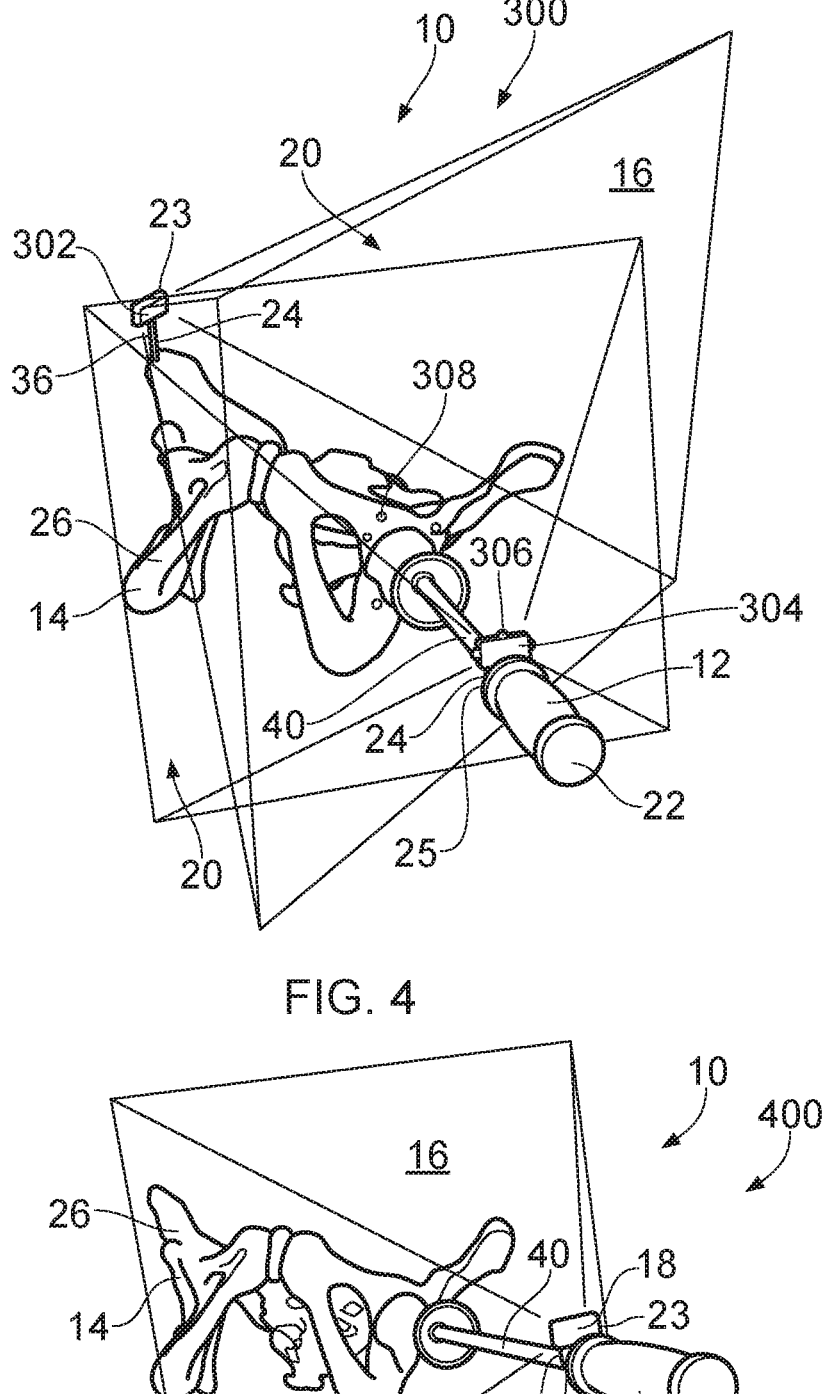
FIG. 4 shows a perspective view of another embodiment of the intraoperative stereotaxic navigation system shown in FIG. 1, in use.
FIG. 5 shows a perspective view of another embodiment of the intraoperative stereotaxic navigation system shown in FIG. 1, in use.

FIG. 4 shows a further embodiment 300 of the system 10 including a pair of the radar-based sensors 18. A first sensor 302 is releasably secured to the patient's bone 14, as previously described, and a second radar-based sensor 304 is releasably secured to the tool 12, as previously described. This embodiment includes two sets of the trackers 38, where a first set of trackers 306 are mounted relative to the second sensor 304, such as directly to the sensor 304 or associated mount 24, to be within the FOV 20 of the first sensor 302, and the second set of trackers 308 are mounted to the patient 26 to be within the FOV 20 of the second sensor 304. The processor 28 is configured to be communicatively connected to both sensors 302, 304 to allow receiving at least one of relative distance, direction, and orientation information relating to any of the trackers 306, 308.

In an alternative arrangement of the embodiment 300, the trackers 306, 308 are absent and instead, one of the first sensor 302 and second sensor 304 is operable to only transmit, not receive, signals. In this scenario, the transmit only sensor 302, 304 effectively provides an active tracker such to allow angular measurement by the other sensor 302, 304, in addition to the other sensor 302, 304 measuring relative distance from signals reflected from the transmit only sensor 302, 304. Operating in this way allows both position and orientation of the transmit only sensor 302, 304 to be determined. In such embodiments, the sensors 302, 304 are configured to communicate with each other to allow calibration, which may then allow determining time of flight of a signal travelling from the transmit only sensor 302 to the other sensor 304.

FIG. 5 shows another embodiment 400 of the system 10 which is substantially identical to the embodiment 200 shown in FIG. 3 but the trackers 38 are omitted. In this embodiment, the processor 28 determines the orientation of the tool 12 responsive to receiving relative distance information relating to the patient's bone 14, such as detecting one or more localised points defined by the bone 14. The sensor 18 is operated to detect signals 27 reflected from the bone 14 to allow determining bone topography by the processor 28, and consequently relative orientation of the tool 12 and bone 14. For example, bony landmarks, such as the anterior superior iliac spines, or ischial tuberosity, may be detected as reflective reference points. In this arrangement, sensor 18 is operable to transmit EM signals 21 through skin and tissue so that the signals 21 are only reflected by bone mass.

Figures 6, 7:
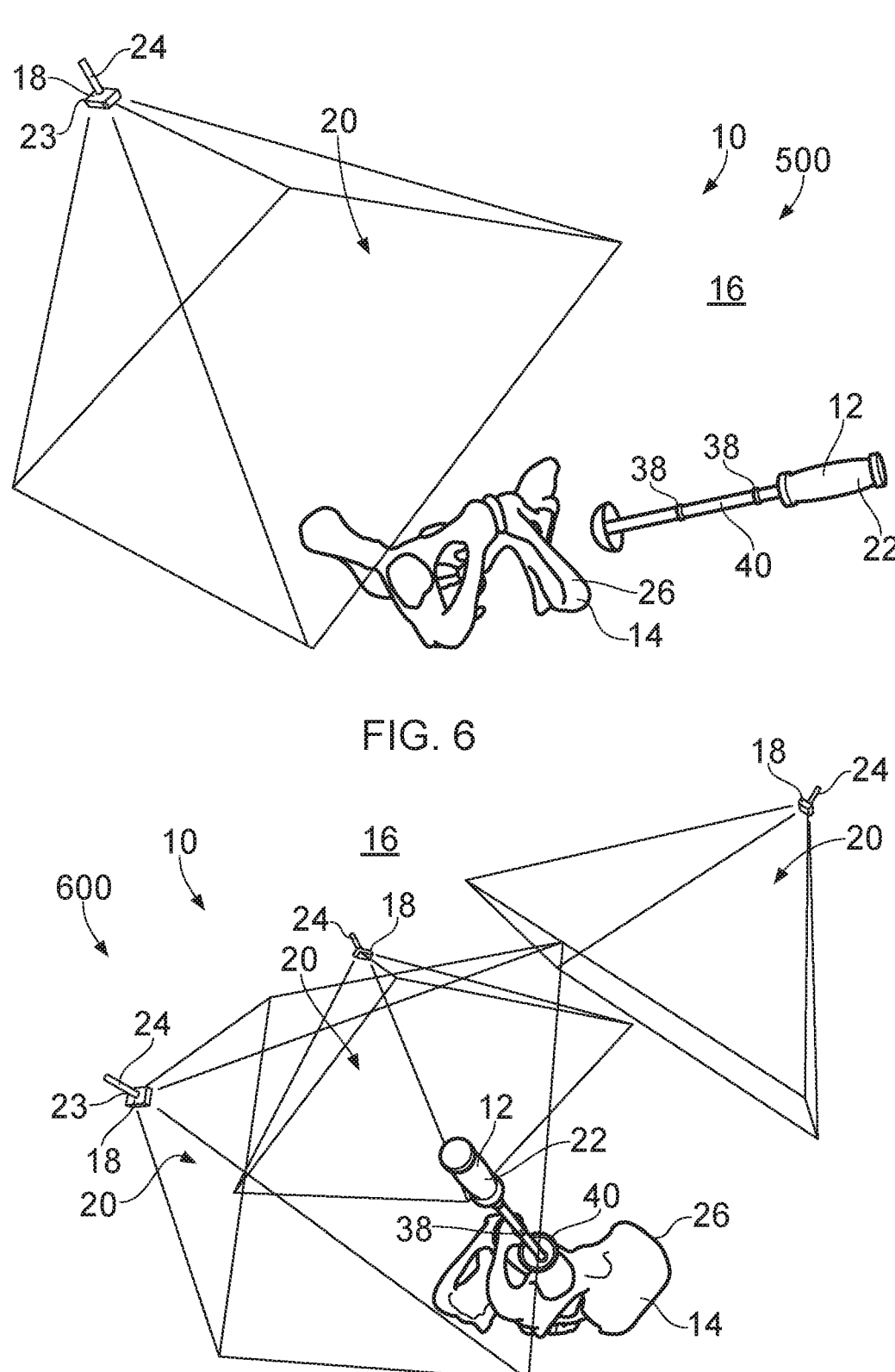
FIG. 6 shows a perspective view of another embodiment of the intraoperative stereotaxic navigation system shown in FIG. 1, in use.
FIG. 7 shows a perspective view of another embodiment of the intraoperative stereotaxic navigation system shown in FIG. 1, in use.

FIG. 6 shows an embodiment 500 of the system 10 which is configured so that the mount 24 secures the radar-based sensor 18 relative to the surgical environment 16, such as fixing the sensor 18 to the ceiling or a wall of a surgical theatre (not shown). Optionally, the trackers 38 are included and configured to be mounted to the patient 26 and/or the tool 12. In this figure, a pair of trackers 38 are mounted to the shaft 40 of the tool 12. The processor 28 is communicatively connected to the sensor 18 and is operable to determine the orientation of the tool 12 responsive to receiving at least one of relative distance, direction, and orientation information relating to one or more points, such as defined by the trackers 38.

For some applications, the sensor 18 is operable so that the transmitted EM signals 21 propagate through the surgical environment. In a further embodiment 600 shown in FIG. 7, the system 10 includes a plurality of the radar-based sensors 18 and respective mounts 24, each sensor 18 communicatively connected to the processor 28. In some embodiments, each of the plurality of radar-based sensors 18 and/or the processor 28 is operable to determine relative spacing between two sensors 18, consequently allowing determining relative position and/or orientation of two or more sensors 18. This usefully provides redundancy in the system 10 to enhance operational scope, for example, in situations where an object, which is impenetrable by the EM signals 21, is placed in front of one of the sensors 18. It will be appreciated that the sensors 18 may be arranged at defined locations within the surgical environment 16, for example, due to the locations defined by direct measurement or from user input.

The system 10 is configured to precisely determine the orientation of a surgical tool 12 relative to the patient's bone 14. This is typically achieved by determining a combination of distance and/or direction from the sensor 18 to one of the bone 14 and tool 12, and determining the orientation of the patient 26 relative to the surgical environment 16. Processing these factors, by the processor 28, consequently allows accurately identifying, and monitoring, the orientation of the tool 12. This orientation information can prove useful to a clinician as this can enhance executing a successful surgical procedure, such as correctly aligning an acetabulum cup with, and inserting into, an acetabulum.

The radar-based sensor 18 is operable to detect movement as small as a fraction of a millimetre due to the high frequency of the transmitted signals 21 and resulting reflected signals 27. Advantageously, this means that use of the system 10 allows for determining, and monitoring, orientation of the tool 12 to within approximately one millimetre accuracy. The accuracy of the system 10 can consequently enhance success of the surgical application to provide improved outcomes for patients 26.

The system 10 is able to determine angular position of the tool 12 by measuring the position of only two points on the tool 12. Processing measurements of only two points reduces computational complexity and, consequently, enhances efficiency of the processor 28. As a result, this can enhance determining orientation of the tool 12 relative to the patient 26.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An intraoperative stereotaxic navigation system for determining an orientation of a surgical tool relative to a patient's bone located within a surgical environment, the system including:

a radar-based sensor comprising a millimetre wave sensor operable to transmit electromagnetic signals having a wavelength in the millimetre range, and receive reflected signals, across a defined field-of-view (FOV) to determine at least one of relative distance to, direction to, and orientation of, one or more objects reflecting signals in the FOV;

a mount configured to releasably secure the radar-based sensor to one of the patient and the surgical tool to allow the other of the patient and the surgical tool to be within the FOV; and a processor communicatively coupled with the radar-based sensor, the processor receives at least one of relative distance, direction, and orientation information relating to at least one of the patient and the surgical tool from the radar-based sensor, and receives patient orientation information relating to the orientation of the patient relative to the surgical environment, the patient orientation information defining at least one vector defined by the patient, and wherein the processor outputs the orientation of the surgical tool relative to the patient's bone based on the relative distance, direction, and/or orientation information, and the patient orientation information.

2. The system of claim 1, wherein the processor is configured to outputs the orientation of the surgical tool responsive to receiving relative distance information and/or direction information from the radar-based sensor, wherein the relative distance and/or direction information relates to one or more points defined by a portion of the patient's bone or the surgical tool.

3. The system of claim 2, wherein at least two points are defined by the patient's bone or the surgical tool, and, wherein, responsive to receiving the relative distance and/or direction information relating to the at least two points, the processor determines a vector defined between the at least two points to determine a position of the patient's bone or the surgical tool.

4. The system of claim 1, further including at least one tracker defining at least one point and configured to be mounted to the patient, the surgical tool, or the surgical environment, and wherein the processor outputs the orientation of the surgical tool based on relative distance information and/or direction information relating to the, at least one tracker.

5. The system of claim 4, wherein at least two points are defined by the at least one tracker, and wherein, responsive to receiving the relative distance and/or direction information relating to the at least two points, the processor determines a vector defined between the at least two points to determine a position of the patient's bone, the surgical tool, or the surgical environment.

6. The system of claim 4, wherein the mount is configured to releasably secure the radar-based sensor to the patient, and the at least one tracker is configured to be mounted to the surgical tool.

7. The system of claim 6, wherein, responsive to receiving the relative distance and/or direction information relating to the at least one tracker, the processor determines at least one of: an orientation of the surgical tool, a velocity of the surgical tool, an acceleration of the surgical tool, an angular displacement of the surgical tool, an angular velocity of the surgical tool, and an angular acceleration of the surgical tool.

8. The system of claim 4, wherein the mount is configured to releasably secure the radar-based sensor to the surgical tool, and the at least one tracker is configured to be mounted to the patient.

9. The system claim 4, comprising a plurality of the trackers, at least some of the trackers being configured to be mounted to the surgical environment, and wherein, responsive to receiving the relative distance and/or direction information relating to the at least some of the trackers, the processor determines the orientation of the patient relative to the surgical environment.

10. The system of claim 4, wherein the, or each, tracker is a reflective marker.

11. The system of claim 4, wherein the mount is configured to releasably secure the radar-based sensor to the patient, and including a further mount configured to releasably secure a further radar-based sensor to the surgical tool, and a plurality of the trackers, wherein at least one tracker is configured to be mounted to one of the further mount and the further radar-based sensor to be within the FOV of the radar-based sensor, and at least one other tracker is configured to be mounted to the patient to be within the FOV of the further radar-based sensor, and wherein the processor is communicatively coupled to the further radar-based sensor to receive relative distance information.

12. The system of claim 1, further including an orientation sensor communicatively coupled to the processor and operable to determine the orientation of the patient relative to the surgical environment.

13. The system of claim 12, wherein the orientation sensor is operable to determine at least two vectors defined by the patient.

14. The system of claim 13, wherein the orientation sensor is releasably securable to one of the radar-based sensor and the mount.

15. The system of claim 13, wherein the orientation sensor and the radar-based sensor are mounted to a common housing.

16. The system of claim 1, further including at least one further radar-based sensor configured to emit signals and be mounted to one of the patient, the surgical tool, and the surgical environment to allow being within the FOV, and wherein the radar-based sensor is operable to receive the signals from the further radar-based sensor, and wherein the processor determines the orientation of the tool responsive to receiving at least one of relative distance information and direction information, from the radar-based sensor, relating to the further radar-based sensor.

17. The system of claim 1, wherein the mount is an integral portion of the, or each, radar-based sensor.

18. The system of claim 1, wherein the surgical tool is an acetabular cup impactor.

* * * * *